(12) United States Patent
Lee

(10) Patent No.: US 8,624,046 B2
(45) Date of Patent: Jan. 7, 2014

(54) KRILL OIL AND METHOD FOR MANUFACTURING THE SAME

(75) Inventor: Sangsu Lee, Gunpo-si (KR)

(73) Assignee: Dae Duck FRD Co., Ltd (KR)

( * ) Notice: Subject to any disclaimer, the term of this patent is extended or adjusted under 35 U.S.C. 154(b) by 0 days.

(21) Appl. No.: 13/976,024

(22) PCT Filed: Jul. 21, 2011

(86) PCT No.: PCT/KR2011/005386
§ 371 (c)(1),
(2), (4) Date: Jun. 25, 2013

(87) PCT Pub. No.: WO2012/108593
PCT Pub. Date: Aug. 16, 2012

(65) Prior Publication Data
US 2013/0274496 A1    Oct. 17, 2013

(30) Foreign Application Priority Data
Feb. 11, 2011 (KR) .................. 10-2011-0012550

(51) Int. Cl.
*C11B 1/00* (2006.01)
*C12P 7/64* (2006.01)
*C12N 1/20* (2006.01)
*C11C 1/00* (2006.01)

(52) U.S. Cl.
USPC ......... 554/18; 435/134; 435/252.31; 435/271

(58) Field of Classification Search
USPC ................ 554/18; 435/134, 252.31, 271
See application file for complete search history.

(56) References Cited

FOREIGN PATENT DOCUMENTS

| KR | 10-1991-0006622 | * | 8/1991 |
|---|---|---|---|
| KR | 19910006622 | | 8/1991 |
| KR | 10-0815118 | * | 3/2008 |
| KR | 100815118 B1 | | 3/2008 |
| KR | 10-2010-0007167 | * | 1/2010 |
| KR | 20100007167 A | | 1/2010 |
| KR | 10-2010-0038029 A | * | 4/2010 |
| KR | 10-0951727 | * | 4/2010 |
| KR | 100951727 B1 | | 4/2010 |
| KR | 20100038029 A | | 4/2010 |
| WO | 2010030193 A | | 3/2010 |
| WO | WO 2010-030193 A1 | * | 3/2010 |

* cited by examiner

Primary Examiner — Deborah D Carr

(57) ABSTRACT

This invention relates to krill oil and a method for manufacturing the same. The method comprises preparing krill, adding protease to the krill and performing enzyme reaction, extracting eicosapentaenoic acid, docosahexaenoic acid, phospholipids, and astaxanthin from the krill after performing the enzyme reaction, and mixing the extracted eicosapentaenoic acid, docosahexaenoic acid, phospholipids, and astaxanthin. The protease may comprise one or more chosen from serine alkaline proteases and metallo neutral proteases. The serine alkaline proteases may comprise proteases separated from *Bacillus licheniformis* and the metallo neutral proteases may comprise proteases separated from *Bacillus subtillis* and *Bacillus amyloliquefaciens*.

10 Claims, 2 Drawing Sheets

KRILL OIL AND METHOD FOR MANUFACTURING THE SAME

BACKGROUND

1. Technical Field

The present disclosure relates to krill oil and a method for manufacturing the krill oil, more particularly, to a method for manufacturing krill oil from krill using proteases and ultra-high pressure reactor and krill oil manufactured by the method.

2. Description of the Related Art

Antarctic krill (*E. superba*) belonging to krill are estimated to have 2 billion tons of inhabitation amount and 30 million tons of fair catch and the world pays attention to the use and development of the krill. The krill as the main prey of marine animals including whales are located in the lowest in the food chain in the Antarctic Ocean and are less polluted, so the krill are very useful in food, cosmetics, pharmaceuticals, etc.

The krill include nutritionally good quality of protein and lipids. The fresh krill include up to about 10% of lipids. The lipids of the krill include about 40% of eicosapentaenoic acid (EPA) and docosahexaenoic acid (DHA), which are omega-3 highly unsaturated fatty acids and about 40~50% of phospholipids. Also, the krill include astaxanthin that is antioxidant of fat soluble carotenoids.

Organic solvent extraction method and supercritical extraction method are used as methods for extracting the lipids, which have high nutritional value, from the krill. The organic solvent extraction method needs a large amount of organic solvent as well as a lot of time for extraction. In addition, when the organic solvent extraction method is used, the organic solvent may not be entirely removed and still remain in krill oil, and wastewater may be produced by the organic solvent. For the supercritical extraction method, supercritical equipment is too expensive and difficult to operate.

SUMMARY

According to some embodiments, the present disclosure provides a method for manufacturing krill oil at low cost. Manufacturing cost can be reduced by extracting effective ingredients of krill not using expensive supercritical equipment and manufacturing krill oil.

According to some embodiments, the present disclosure also provides a method for manufacturing krill oil eco-friendly. The krill oil can be manufactured by extracting the effective ingredients of the krill eco-friendly not using toxic organic solvents such as acetone, hexane, etc.

In addition, the present disclosure provides krill oil manufactured using the above method.

According to some embodiments, the present disclosure provides a method for manufacturing krill oil comprising preparing krill, adding protease to the krill and performing enzyme reaction, extracting eicosapentaenoic acid, docosahexaenoic acid, phospholipids, and astaxanthin from the krill after performing the enzyme reaction, and mixing the extracted eicosapentaenoic acid, docosahexaenoic acid, phospholipids, and astaxanthin. The protease may comprise one or more chosen from serine alkaline proteases and metallo neutral proteases. The serine alkaline proteases may comprise proteases separated from *Bacillus licheniformis* and the metallo neutral proteases may comprise proteases separated from *Bacillus subtillis* and *Bacillus amyloliquefaciens*.

The enzyme reaction may be performed in an ultra-high pressure reactor. In the ultra-high pressure reactor, reaction pressure is 10~300 MPa, reaction temperature is 50~60° C., and reaction time is 3~24 hours. In the ultra-high pressure reactor, the krill including the protease are liquefied.

After performing the enzyme reaction, the pH of the liquefied krill may be adjusted to be 3.0~5.0.

After performing the enzyme reaction, the liquefied krill may be filtered to be separated as filtrate and sludge, the eicosapentaenoic acid, the docosahexaenoic acid, and the phospholipids may be extracted by centrifugation of the filtrate, and the astaxanthin may be extracted by cleaning the sludge with ethanol.

The preparing of the krill may comprise pulverizing the krill.

Before performing the enzyme reaction, the pH of the krill is adjusted to be 7.5~9.0.

According to some embodiments, the present disclosure provides krill oil manufactured by the method. The krill oil may comprise 14~18 wt % of eicosapentaenoic acid, 8~12 wt % of docosahexaenoic acid, 35~45 wt % of phospholipids, and 70~170 ppm of astaxanthin.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF SPECIFIC EMBODIMENTS

Hereinafter, a detailed description will be given of embodiments of the present invention. The present invention is not limited to these embodiments and may be embodied in the other forms. The embodiments of the present invention are provided so that thorough and complete contents are ensured and the spirit of the invention is sufficiently transferred to a person having ordinary knowledge in the art.

Figure 1:
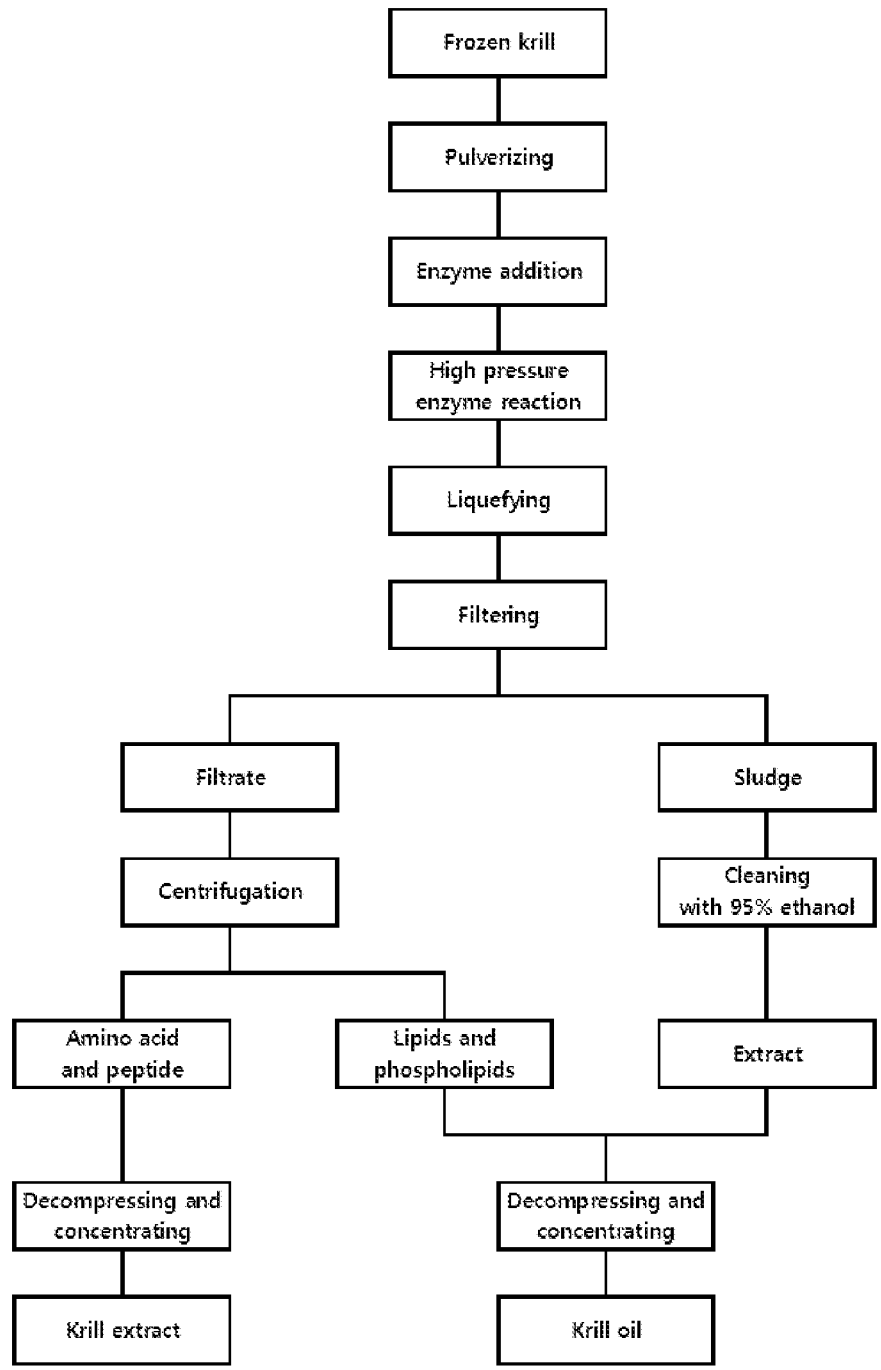
FIG. 1 illustrates a process for manufacturing krill oil according to an embodiment of the present invention.

FIG. 1 illustrates a process for manufacturing krill oil according to an embodiment of the present invention.

Referring to FIG. 1, frozen or freeze-dried krill are thawed and salt is removed from the krill by washing. The krill are pulverized. The krill may be pulverized as a size of about 0.5 cm.

Protease is added to the pulverized krill. The protease and the krill may be mixed and stirred for 30 min~1 hr. The protease may comprise one or more chosen from serine alkaline proteases and metallo neutral proteases. The serine alkaline proteases may comprise proteases separated from *Bacillus licheniformis*. The metallo neutral proteases may comprise proteases separated from *Bacillus subtillis* and *Bacillus amyloliquefaciens*. The present inventors have conducted many experiments using various proteases and have found that lipids, phospholipids, and astaxanthin can be effectively extracted from krill by the serine alkaline proteases separated from *Bacillus licheniformis* and/or the metallo neutral proteases separated from *Bacillus subtillis* and *Bacillus amyloliquefaciens*.

The protease may be added in an amount of 0.1~3.0 parts by weight parts per 100 parts by weight of the krill. In case where an addition amount of the protease is less than 0.1 parts by weight, the amount of the protease is too low compared to the amount of protein of the krill, so enzyme reaction may be delayed or hydrolysis of the protein may be incomplete. In case where an addition amount of the protease is more than 3.0 parts by weight, the hydrolysis of the protein may be fast but the protease is added than necessary compared to the amount of the protein so over-use of the protease may have a bad influence on flavor of the krill and manufacturing costs may increase.

After adding the protease to the krill, the pH of the krill may be adjusted to be 7.5~9.0. The protease may be activated in the range of the above pH.

Enzyme reaction is performed in the krill. Protein of the krill can be hydrolyzed by the enzyme reaction. The enzyme reaction may be performed in an ultra-high pressure reactor. In the ultra-high pressure reactor, the reactor pressure may be 30~300 MPa, the reactor temperature may be 50~60° C., and the reaction time may be 3~24 hours. In the ultra-high pressure reactor, the krill can be liquefied and the enzyme reaction can be performed in the liquefied krill.

After performing the enzyme reaction, the pH of the liquefied krill may be adjusted to be 3.0~5.0. The pH can be adjusted by adding 2~4 parts by weight of citric acid and/or ascorbic acid per 100 parts by weight of the krill and letting the krill be stationary for 30 min~1 hr. A mixture of water and amino acids formed by the hydrolysis of the protein and lipids can be separated each other by adjusting the pH.

After performing the enzyme reaction, the liquefied krill are filtered to be separated as filtrate and sludge.

The filtrate is filtered using 100 and 200 mesh sieve and the sludge including the shell of the krill and so on can be separated.

The filtrate is centrifuged and lipids and phospholipids can be extracted. The lipids may comprise eicosapentaenoic acid (EPA) and docosahexaenoic acid (DHA). The centrifugation speed may be 3000~13000 rpm. The amino acids and peptides can be collected from the filtrate by the centrifugation. Krill extract can be manufactured by decompressing and concentrating the amino acids and the peptides.

The sludge is cleaned with 95% ethanol and astaxanthin can be extracted. The ethanol may be added in the amount of 200~300 parts by weight per 100 parts by weight of the sludge.

Krill oil can be manufactured by mixing the lipids, the phospholipids and the astaxanthin and by decompressing and concentrating them. The ethanol can be collected and the water can be removed in the decompressing and concentrating process. The temperature in the decompressing and concentrating process may be 45~65° C.

Figure 2:
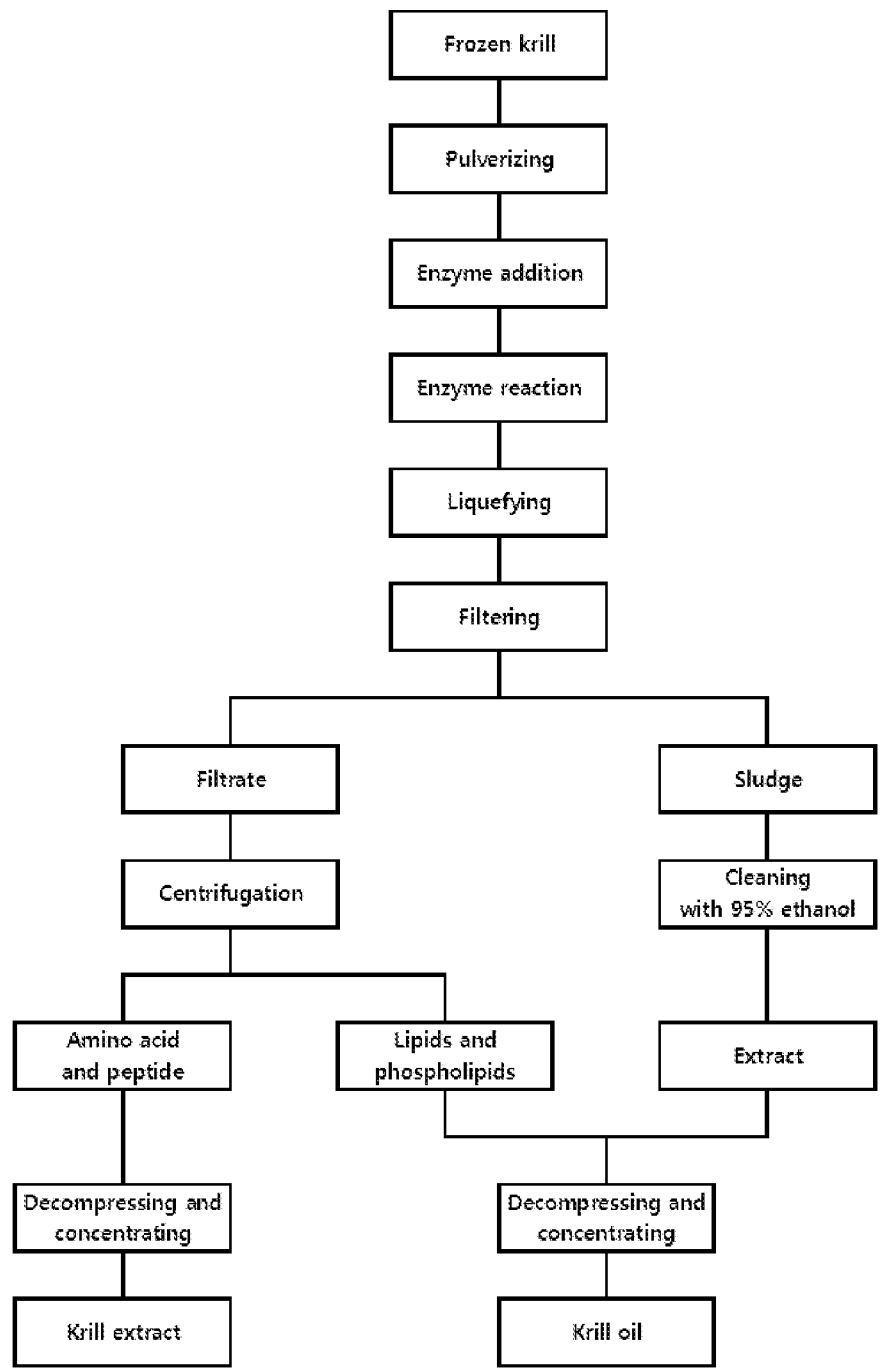
FIG. 2 illustrates a process for manufacturing krill oil according to other embodiment of the present invention.

FIG. 2 illustrates a process for manufacturing krill oil according to other embodiment of the present invention. Referring to FIG. 2, the enzyme reaction may be performed in a conventional reactor rather than the ultra-high pressure reactor.

EXAMPLES

Preparation of Krill

Krill were prepared by thawing frozen krill and washing the thawed krill with water to remove salt and impurities and freeze-dried krill were prepared. The analysis of the nutritional composition is shown in Table 1 below.

TABLE 1

| Ingredient | Frozen krill (g/100 g) | Freeze-dried krill (g/100 g) |
|---|---|---|
| Water | 75.5 | 5.5 |
| Lipids | 7.3 | 20.3 |

TABLE 1-continued

| Ingredient | Frozen krill (g/100 g) | Freeze-dried krill (g/100 g) |
|---|---|---|
| Protein | 12.5 | 61.4 |
| Ash | 4.7 | 12.8 |

Manufacture Of Krill Oil

Examples 1 to 4

Krill samples were prepared by pulverizing frozen krill with a mixer. Distilled water and proteases were added to the krill samples. The krill samples were hydrolyzed at the ultra-high pressure of 30, 50, 70, and 100 MPa and at the temperature of 55° C. and were liquefied. Mixed liquid of serine alkaline proteases separated from *Bacillus licheniformis* and metallo neutral proteases separated from *Bacillus subtillis* and *Bacillus amyloliquefaciens* was used as the above proteases. The serine alkaline proteases and the metallo neutral proteases may be separated by low-temperature water extraction method.

The distilled water was added in the amount of 100 parts by weight and the proteases were added in the amount of 1 parts by weight per 100 parts by weight of the krill.

After performing the hydrolyzation, the hydrolyzed and liquefied products were filtered to be separated as filtrate and sludge. The filtrate was centrifuged and lipids and phospholipids were extracted. The sludge was cleaned with ethanol and astaxanthin was extracted. Krill oil was manufactured by mixing the lipids, the phospholipids and the astaxanthin and by decompressing and concentrating them. The recovery ratios of the lipids are shown in Table 2 below.

TABLE 2

| | Pressure of ultra-pressure reactor | | | |
|---|---|---|---|---|
| Reaction time (hours) | 30 MPa Example 1 (%) | 50 MPa Example 2 (%) | 70 MPa Example 3 (%) | 100 MPa Example 4 (%) |
| 0 | 0 | 0 | 0 | 0 |
| 3 | 28 | 32 | 40 | 37 |
| 6 | 55 | 60 | 72 | 67 |
| 9 | 70 | 82 | 92 | 88 |
| 12 | 88 | 90 | 95 | 92 |
| 15 | 93 | 93 | 95 | 95 |
| 18 | 95 | 95 | 95 | 95 |
| 21 | 95 | 95 | 95 | 95 |
| 24 | 95 | 95 | 95 | 95 |

As presented in Table 2, when the reaction time was more than 3 hours, the recovery ratios of the lipids were more than 30%. When the reaction time was more than 9 hours, the recovery ratios of the lipids were more than 80%. When the reaction time was more than 12 hours, the recovery ratios of the lipids were more than 90%. When the reaction time was more than 18 hours, the recovery ratios of the lipids were more than 95% regardless of the size of the pressure.

Example 5

Krill samples were prepared by pulverizing frozen krill with a mixer. Distilled water and proteases were added to the krill samples. The krill samples were hydrolyzed for 12 hours at atmospheric pressure and at the temperature of 55° C. and were liquefied. Mixed liquid of serine alkaline proteases separated from *Bacillus licheniformis* and metallo neutral proteases separated from *Bacillus subtillis* and *Bacillus amyloliquefaciens* was used as the above proteases.

The distilled water was added in the amount of 100 parts by weight and the proteases were added in the amount of 1 parts by weight per 100 parts by weight of the krill.

After performing the hydrolyzation, the hydrolyzed and liquefied products were filtered to be separated as filtrate and sludge. The filtrate was centrifuged and lipids and phospholipids were extracted. The sludge was cleaned with ethanol and astaxanthin was extracted. Krill oil was manufactured by mixing the lipids, the phospholipids and the astaxanthin and by decompressing and concentrating them.

Example 6

Krill samples were prepared by pulverizing frozen krill with a mixer. Distilled water was added to the krill samples. The krill samples were hydrolyzed for 12 hours at the ultra-high pressure of 100 MPa and at the temperature of 55° C. and were liquefied. The distilled water was added in the amount of 100 parts by weight per 100 parts by weight of the krill. Proteases were not added unlike the above Example 5 and krill oil was manufactured using an ultra-high pressure reactor.

Example 7

Krill samples were prepared by pulverizing frozen krill with a mixer. Distilled water and proteases were added to the krill samples. The krill samples were hydrolyzed for 12 hours at the ultra-high pressure of 100 MPa and at the temperature of 55° C. and were liquefied. Krill oil was manufactured by the same method as the above Example 5 except using an ultra-high pressure reactor.

Example 8

Krill samples were prepared by pulverizing freeze-dried krill with a mixer. Distilled water and proteases were added to the krill samples. The krill samples were hydrolyzed for 12 hours at the ultra-high pressure of 100 MPa and at the temperature of 55° C. and were liquefied. Krill oil was manufactured by the same method as the above Example 7 except using the freeze-dried krill.

Nutritional composition of the krill oil manufactured in the above Examples 5 to 8 was analyzed. The results are shown in Table 3 below. The analysis method for the nutritional composition is as follows.

(a) Fatty acid analysis: Krill oil was hydrolyzed with methanolic NaOH. Methyl esterification was performed with fatty acid derivatization reagent for the hydrolyzed krill oil and gas chromatography analysis was performed.

(b) Lipid analysis: According to the lipid analysis method of Health Functional Food Code, neutral lipids and impurities were removed from krill oil with hexane. Lipids were measured as acetone insoluble material by dissolving the krill oil in acetone.

(c) Astaxanthin analysis: According to the astaxanthin analysis method of Test Manual for Health Functional Food Funcion and Indicator, krill oil was hydrolyzed with cholesterol esterase, and then dissolved in petroleum ether. After concentrating the petroleum ether and redissolving with acetone, liquid chromatography (HLPC) analysis was performed.

TABLE 3

| Example | Extraction method | Lipids (g) | Recovery ratio (%) | EPA (%) | DAH (%) | Phospholipids (mg/g) | Astaxanthin (ppm) |
|---|---|---|---|---|---|---|---|
| Example 5 | Enzyme reaction | 6.14 | 84 | 15.3 | 8.2 | 38.2 | 74 |
| Example 6 | Ultra-high pressure reaction | 5.89 | 81 | 14.5 | 7.4 | 32.6 | 75 |
| Example 7 | Ultra-high pressure enzyme reaction | 6.94 | 95 | 17.5 | 10.1 | 44.7 | 172 |
| Example 8 | Ultra-high pressure enzyme reaction | 19.28 | 95 | 17.8 | 11.2 | 43.9 | 169 |

As presented in Table 3, in Examples 5 and 6 using proteases or ultra-high pressure reactor, the recovery ratios of the lipids were above 80%. In Examples 7 and 8 using both of the proteases and the ultra-high pressure reactor, the recovery ratios of the lipids were very high as 95% and the content of the astaxanthin was very high. The krill oil may comprise 14~18 wt % of eicosapentaenoic acid, 8~12 wt % of docosahexaenoic acid, 35~45 wt % of phospholipids, and 70~170 ppm of astaxanthin.

The foregoing is illustrative of embodiments of the present invention and is not to be construed as limiting of the present invention. Although a few example embodiments have been described, those skilled in the art will readily appreciate that many modifications are possible in the example embodiments without materially departing from the novel teachings and advantages of the present invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of embodiments of the present invention and is not to be construed as limited to the specific example embodiments disclosed, and that modifications to the disclosed example embodiments, as well as other example embodiments, are intended to be included within the scope of the appended claims. The present invention is best defined by the following claims, with equivalents of the claims to be included therein.

What is claimed is:

1. A method for manufacturing krill oil, the method comprising:
   preparing krill;
   adding protease to the krill and performing enzyme reaction;
   extracting eicosapentaenoic acid, docosahexaenoic acid, phospholipids, and astaxanthin from the krill after performing the enzyme reaction; and
   mixing the extracted eicosapentaenoic acid, docosahexaenoic acid, phospholipids, and astaxanthin,
   wherein the protease comprises one or more chosen from serine alkaline proteases and metallo neutral proteases.

2. The method of claim 1, wherein the enzyme reaction is performed in an ultra-high pressure reactor.

3. The method of claim 2, wherein in the ultra-high pressure reactor, reaction pressure is 10~300 MPa, reaction temperature is 50~60° C., and reaction time is 3~24 hours.

4. The method of claim 3, wherein in the ultra-high pressure reactor, the krill including the protease are liquefied.

5. The method of claim 4, wherein after performing the enzyme reaction, the pH of the liquefied krill is adjusted to be 3.0~5.0.

6. The method of claim 5, wherein after performing the enzyme reaction, the liquefied krill are filtered to be separated as filtrate and sludge,
   the eicosapentaenoic acid, the docosahexaenoic acid, and the phospholipids are extracted by centrifugation of the filtrate, and
   the astaxanthin is extracted by cleaning the sludge with ethanol.

7. The method of claim 1, wherein the preparing of the krill comprises pulverizing the krill.

8. The method of claim 1, wherein before performing the enzyme reaction, the pH of the krill is adjusted to be 7.5~9.0.

9. Krill oil, wherein the krill oil is manufactured by the method of claim 1 and comprises 14~18 wt % of eicosapentaenoic acid, 8~12 wt % of docosahexaenoic acid, 35~45 wt % of phospholipids, and 70~170 ppm of astaxanthin.

10. The method of claim 1, wherein the serine alkaline proteases comprise proteases separated from *Bacillus licheniformis* and the metallo neutral proteases comprise proteases separated from *Bacillus subtillis* and *Bacillus amyloliquefaciens*.

* * * * *